United States Patent [19]
Kraft et al.

[11] Patent Number: 5,508,521
[45] Date of Patent: Apr. 16, 1996

[54] METHOD AND APPARATUS FOR DETECTING LIQUID PRESENCE ON A REFLECTING SURFACE USING MODULATED LIGHT

[75] Inventors: Clifford H. Kraft, Naperville, Ill.; Gregory S. Godlevski; David T. Bach, both of Raleigh, N.C.

[73] Assignee: Cardiovascular Diagnostics Inc., Raleigh, N.C.

[21] Appl. No.: 349,411

[22] Filed: Dec. 5, 1994

[51] Int. Cl.$^6$ .......................... G01N 15/06; G01N 21/49; G01N 21/85

[52] U.S. Cl. .................. 250/574; 250/576; 250/341.8; 250/339.11; 250/559.4

[58] Field of Search ................... 250/574, 576, 250/341.8, 339.11, 559.4

[56] References Cited

U.S. PATENT DOCUMENTS

| | | | |
|---|---|---|---|
| 4,315,159 | 2/1982 | Niwa et al. | 250/578 |
| 4,591,710 | 5/1986 | Komadina et al. | 250/221 |
| 4,723,319 | 2/1988 | Stricker | 455/161 |
| 4,849,340 | 7/1989 | Oberhardt . | |
| 5,110,727 | 5/1992 | Oberhardt . | |
| 5,117,099 | 5/1992 | Schmidt | 250/208.2 |
| 5,177,565 | 1/1993 | Stoughton | 356/446 |
| 5,406,082 | 4/1995 | Pearson et al. | 250/341.8 |

*Primary Examiner*—Edward P. Westin
*Assistant Examiner*—Jacqueline M. Steady
*Attorney, Agent, or Firm*—Clifford Kraft

[57] ABSTRACT

The invention is a Method and Apparatus for detecting the application of a liquid drop into a transparent reaction chamber or other reflecting surface in the presence of ambient light and transient motion of the chamber. A light source is modulated into two or more discrete levels at a fixed or variable modulation rate. These levels include an off level where there is no light from the optical source. Light from the source is specularly reflected into an optical detector which is sampled at least once for each modulated light level. Differences between modulated levels and the off level represent the amount of reflectivity of the surface or chamber. When liquid enters the chamber or is applied to the surface, the reflectivity changes. This leads to detectable changes between the modulated levels and the off level. Ambient light simply shifts the absolute values of the levels. The amplitude differences are compared against thresholds to determine if the reflectivity has changed sufficiently to indicate the presence of liquid. If such a detection occurs for three or more complete modulation cycles, the presence of liquid is reported.

14 Claims, 6 Drawing Sheets

METHOD AND APPARATUS FOR DETECTING LIQUID PRESENCE ON A REFLECTING SURFACE USING MODULATED LIGHT

BACKGROUND

1. Field of the Invention

This invention relates generally to the field of detection of a change in reflected light in the presence of ambient light, and more particularly to the detection of the application of liquid to a reflecting surface or reaction chamber having a highly reflecting surface using modulated light.

2. Description of the Related Art

In various biomedical applications, it is very desirable to be able to detect when the level of reflected light from a surface has changed. This is particularly useful when it is desired to detect the application of liquid to a reaction chamber such as that described by Oberhardt in U.S. Pat. Nos. 4,849,340 and 5,110,727.

In order to accurately measure a time duration between the start of a biochemical reaction and its endpoint in the reaction chamber, the beginning time of the reaction must be accurately known. In the types of reactions taught by Oberhardt, the start time occurs when a drop of blood or serum is placed into the chamber. This application of liquid causes the chamber to take on a different index of refraction or a different absorption. Either of these, causes a reflected beam of light to change amplitude.

Previous methods of detecting this change simply looked for an increase or decrease in reflected light level whose absolute value was greater than a certain fixed threshold. These methods are very susceptible to false triggering from changes in ambient light reaching the detector and from vibration or movement of the chamber. For example, flashes of light, or changes in shadows entering the detector, could cause the system to false trigger and start the reaction timing prematurely. Also, when the reaction chamber is mounted on a card of some sort for backing, and the card is slightly moved with respect to the light source or detector, a false trigger can occur. Such motion can occur when a blood dispenser such as DIFF-SAFE (R) made by Alpha Scientific Corp. of Southeastern, Pennsylvania. inserted into a Vacutainer (R) made by Becton Dickinson of Rutherford, N.J. is touched to the surface of the test card prior to dispensing a drop of blood or serum.

It would be extremely desirable to have a detection method that is very sensitive to changes in reflected light but very insensitive to changes in ambient light and insensitive to vibration or transient motion of the reflective surface.

SUMMARY OF THE INVENTION

The present invention comprises a method and apparatus for detecting the application of a liquid drop into a transparent reaction chamber or other reflecting surface in the presence of static or changing ambient light conditions and transient motion of the chamber.

A light source is modulated into two or more discrete levels at a fixed or variable modulation rate. These levels include an off level where there is no light emitted from the source. The light from the source is reflected from a reflecting surface to an optical detector. The output of this detector is sampled sequentially at least once for each modulated level.

The sample values from the detector representing the off level are proportional to the amount of ambient light entering the system. Differences between other modulated levels and the off level represent the amount of reflectivity of the surface or chamber. When liquid enters the chamber, or is applied to the surface, the reflectivity changes because of a difference in index of refraction or a difference in absorption. This leads to changes in the differences between the on levels and the off level even in the presence of large amounts of ambient light. However, ambient light alone will not produce changes in the differences, but simply shift all the levels up or down in amplitude.

The amplitude differences are compared against thresholds to determine if the reflectivity has changed sufficiently to indicate that the liquid has been applied. If more than one difference has changed sufficiently, the system reports that the liquid has been detected.

Since there may be the possibility of long term drift, running averages may be kept of the differences, and changes in differences can be compared against these averages rather than some original absolute value.

Also, since large reflections or ambients may drive the optical detection system into saturation on the brightest modulated level, the invention can sense this condition and discount changes of one or more of the differences.

BRIEF DESCRIPTION OF THE DRAWINGS

For a more complete understanding of this invention, reference should now be made to the embodiments illustrated in greater detail in the accompanying drawings and described below by way of examples of the invention.

It should be understood that the invention is not necessarily limited to the particular embodiments illustrated herein.

DESCRIPTION OF PREFERRED EMBODIMENTS

Figure 1:
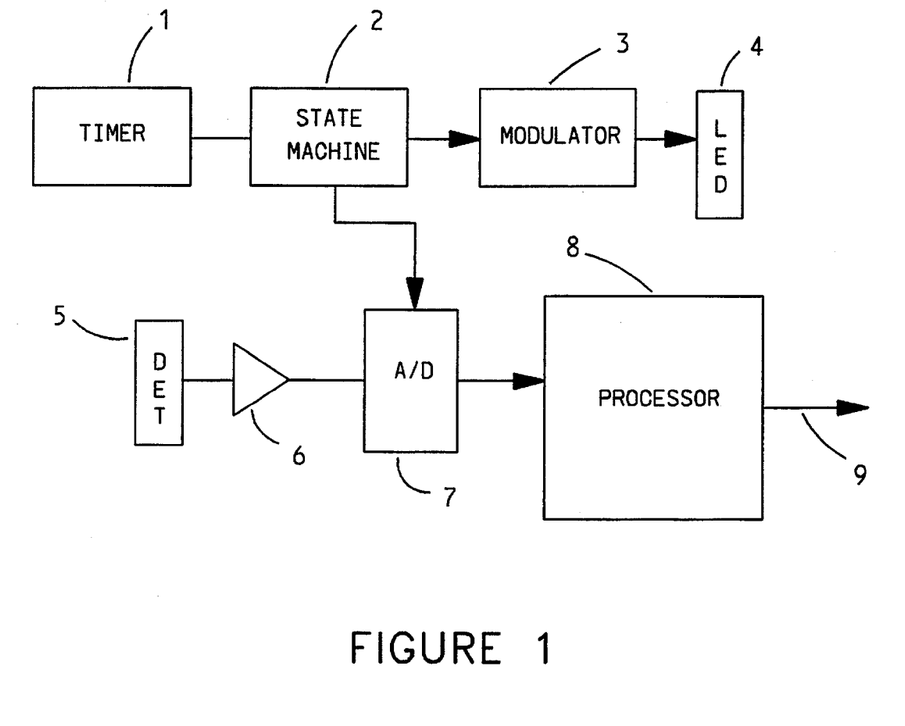
FIG. 1 is a block diagram of the invention.

FIG. 1 is a block diagram of the invention. A timer 1 produces a periodic signal at some predetermined repetition rate. This timer 1 can be of type 555 well known in the digital art for producing periodic signals, or it can be any other type of astable oscillator capable of producing a periodic signal.

Repetition rates of between 400 Hz and 1200 Hz have been found satisfactory. If a rate of about 833 Hz is used, the modulation rate of the invention becomes 10 mS as will be explained.

The timer 1 drives a programmable logic device (PLD) state machine 2 that produces a set of control signals. This state machine can be realized in discrete logic, by an integrated circuit, or any other digital method. These control signals drive a modulator 3 that controls an optical source 4 similar to an infrared LED of the type OP290 manufactured by TRW Electronic Components Group. Other wavelengths can be used besides infrared. The optical source is driven so that it produces an off level (no light), and at least one on level. It has been found that two on levels provide not only adequate detection of the application of liquid in the presence of ambient light, but also are able to function of a wide dynamic range of ambient and reflected light levels.

Light from the LED 4 reflects from the surface in question back to an optical detector such as a PIN diode of the type BP104BS manufactured by Siemens Corp. Any optical detector can be used that is responsive to the light from the optical source 4. The current output of the optical detector is converted to voltage and amplified by a transconductance amplifier well known in the art. This voltage signal is supplied to the analog input of an A/D converter 7. While one embodiment of the invention uses a PIN diode as an optical detector, any other type of optical detector known in the art will work, including a photomultiplier, linear array, or photodetector. A light to frequency converter similar to the TSL230 manufactured by Texas Instruments may also be used in a similar circuit.

The A/D converter can be a 10 or 12 bit converter that converts at rates of 100 kHz or faster. A/D converters are well known in the data acquisition art. A parallel unit such as the ADC12062 manufactured by National Semiconductor can be used as well as a serial unit such as the MAX186 manufactured by Maxim Integrated Products. If a light to frequency converter is used, the A/D can be omitted without changing the invention.

The A/D converter is synchronized to the state machine 8 so that it converts once for each different modulated light level. Its digital output is coupled to a processor 8 which can be any microprocessor or microcontroller known in the art. This processor 8 executes a program that takes differences between the modulated levels and the off level, evaluates the off level for presence of ambient light, computes running averages, and compares the differences against thresholds to decide when liquid has been applied to the reflecting surface or reaction chamber.

The processor 8 can be coupled to a port 9 that reports the detection of liquid, or it can simply continue another program (such as timing a biochemical reaction) when the detection is made. After detection, the modulator can be adjusted to cause the optical source to output a fixed light level for other applications.

It is possible to control the light level of the modulator directly from the processor 8 through standard input/output ports known in the art. In such an alternative embodiment, the function of the state machine is simulated in the processor's program. The processor can also control the timing and initiation of A/D conversions.

Figure 2:
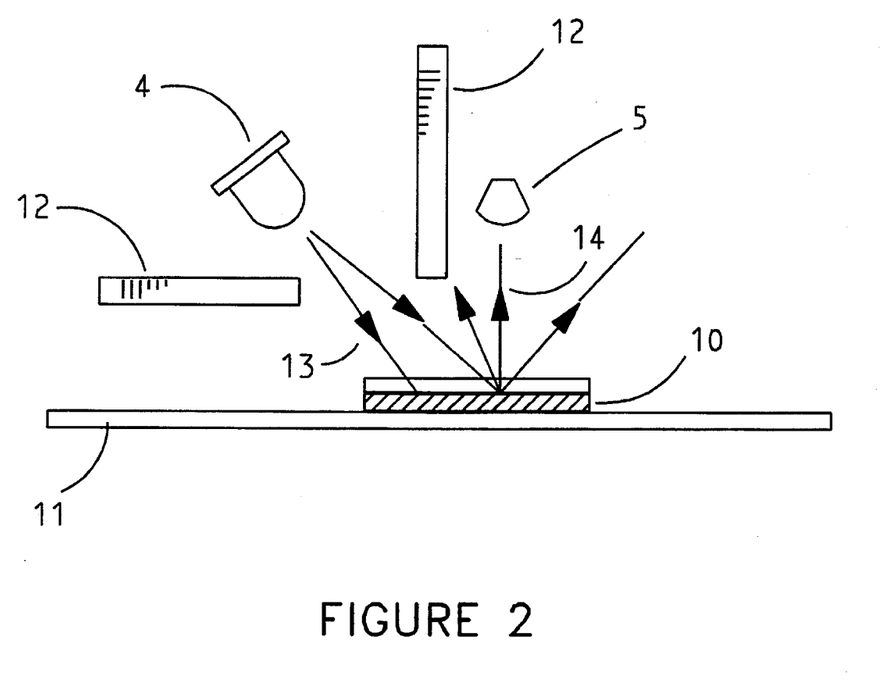
FIG. 2 shows the optical source, reflecting surface which is part of a reaction chamber, and optical detector.

FIG. 2 shows the optical source 4 that produces light that passes through an aperture in an opaque surface 12 and onto a reflecting surface or reaction chamber 11 with a transparent cover 10. Light from the source 13 reflects off the surface 11. The specular reflected rays 14 pass into the optical detector 5 through a second aperture in the opaque surface 12.

Figure 3:
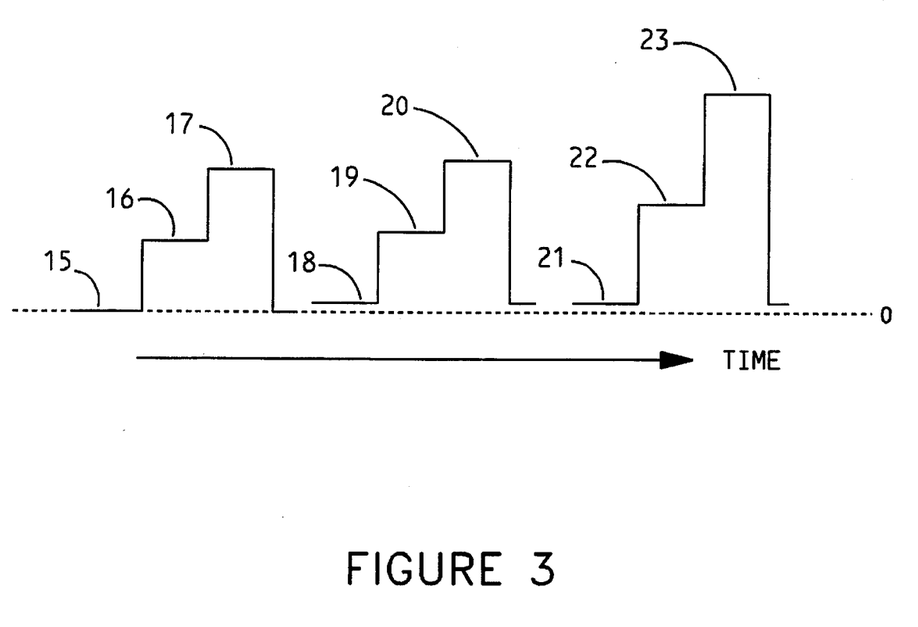
FIG. 3 is a timing diagram of sampled light levels from a three-state modulator in the presence of ambient light.

FIG. 3 shows levels of modulated light as they would appear at the output of the transconductance amplifier 6 (FIG. 1). In this embodiment, three modulation levels are used: one off level 15, and two on levels 16 and 17. The first on level 16 represents a medium bright state where the optical source is about half on. The second on level 17 represents a bright state where the optical source is almost full on. After the bright state 17, the sequence repeats indefinitely. A time for each level should be between 5 mS and 20 mS. In practice, 10 mS functions satisfactorily. Any other sequence of light levels can be used in the invention as long as one of the levels is an off level of the optical source (no light).

When ambient light enters the system, the off level as detected at the optical detector shifts up in amplitude 18. The value of this measured off level is directly proportional to all ambient entering the detector. The other two levels 19 and 20 also shift up, but the difference between level 19 and the off level 18 and the difference between level 20 and the off level remain approximately constant.

When liquid enters the chamber or is present upon the reflecting surface, the differences change significantly. Levels 21, 22, and 23 represent the detected signal in the presence of the same amount of ambient light as the levels 18, 19, and 20, but with liquid in the chamber. It can be clearly seen that the difference between level 23 and level 21 is greater than the difference between level 20 and level 18. The same holds for the difference between level 22 and level 21 compared to the difference between level 19 and level 18. This change of differences is used to detect the presence of liquid on the reflecting surface. It should be noted that with various types of liquids, the differences may either increase as shown in FIG. 3 or they may decrease (not shown). Thus, the absolute values of the differences must be considered and compared to thresholds for detection.

Figure 4:
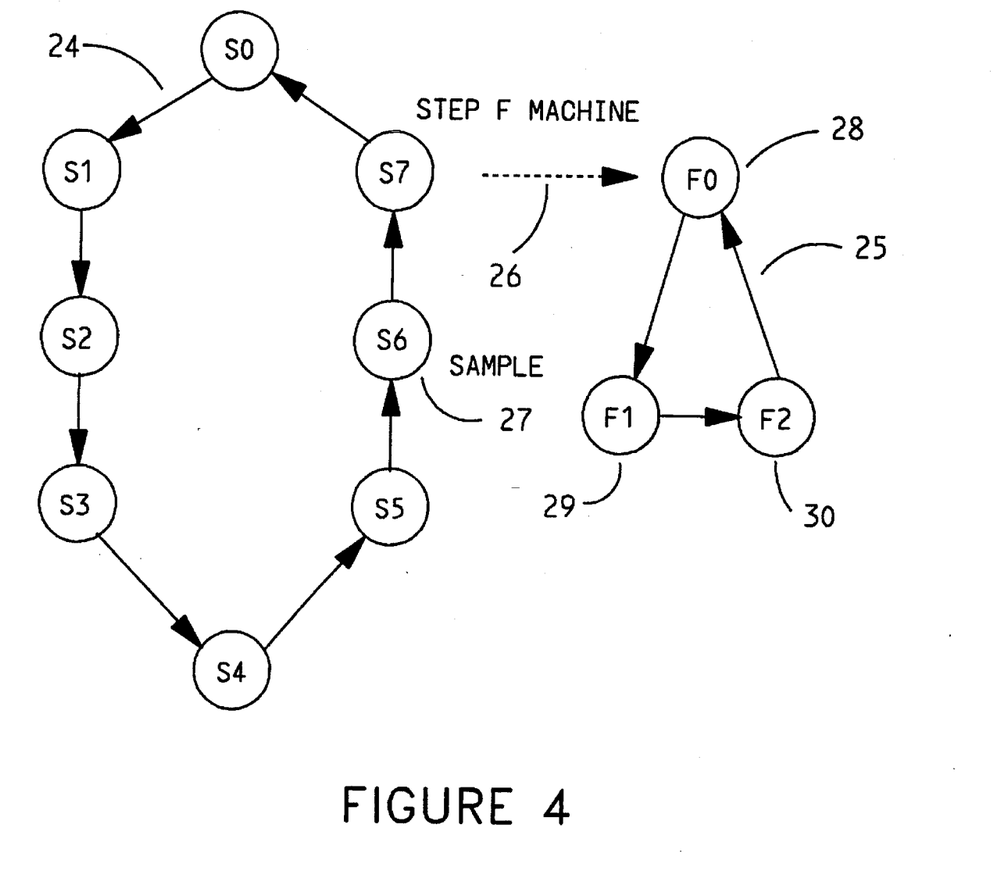
FIG. 4 is a state diagram of an embodiment of the modulator.

FIG. 4 is a state diagram of the state machine 2 (FIG. 1) that may be used to control the modulation. It is driven by the periodic output of the timer 1 (FIG. 1). At each rising edge of the periodic signal, the state machine labeled S0 through S7 24 advances one state. If the periodic signal is about 833 Hz, the S0–S7 state machine 24 makes one complete cycle in about 10 mS. The state machine 24 is a Mealy Machine known in the art in the sense that as it leaves state 7, it causes a second state machine labeled F0–F3 25 to advance one state. Thus, for every cycle of the S0–S7 machine 24, the F0–F3 machine 25 advances one step. The F0–F3 machine 25 makes one complete cycle for every three complete cycles of the S0–S7 machine 24. The F0–F3 machine 25 thus completes a cycle in about 30 mS if the periodic signal from the timer 1 (FIG. 1) is about 833 Hz.

The S0–S7 state machine may signal the A/D to convert as it passes through state S6 27. It can output this convert command signal either as a Moore Machine (output with state) or a Mealy Machine (output with state transition), both well known in the digital art.

The state machine F0–F3 25 can drive two control lines to the modulator 3 (FIG. 1). These control lines are such that in state F0 28, the optical source is off; in state F1 29, it is at medium brightness, and in state F2 30, it is at full brightness. The state machine F0–F3 25 thus controls the amount of light leaving the optical source and hence the amount of light arriving at the optical detector.

The state machines shown in FIG. 4 are merely representative of the type of controller needed to drive the modulator. This particular example causes the modulator to possess three brightness states that occur in order of increasing brightness. Other state machines and modulation schemes are included in the invention. It is possible to use any number of brightness levels and to sequence them in any order. It is not necessary that they all be of the same duration. The important feature of the invention is that one of the levels represents the off state of the optical source. It is this level that provides information on the amount of ambient light entering the optical detector.

The state machine shown in FIG. 4 or any state machine that could control the modulator can be programmed into a PLD of the type 22V10 manufactured by Cypress Semiconductors or equivalent. It could also be constructed from discrete integrated circuits or components, or it could be itself a microprocessor or microcontroller.

Figure 5:
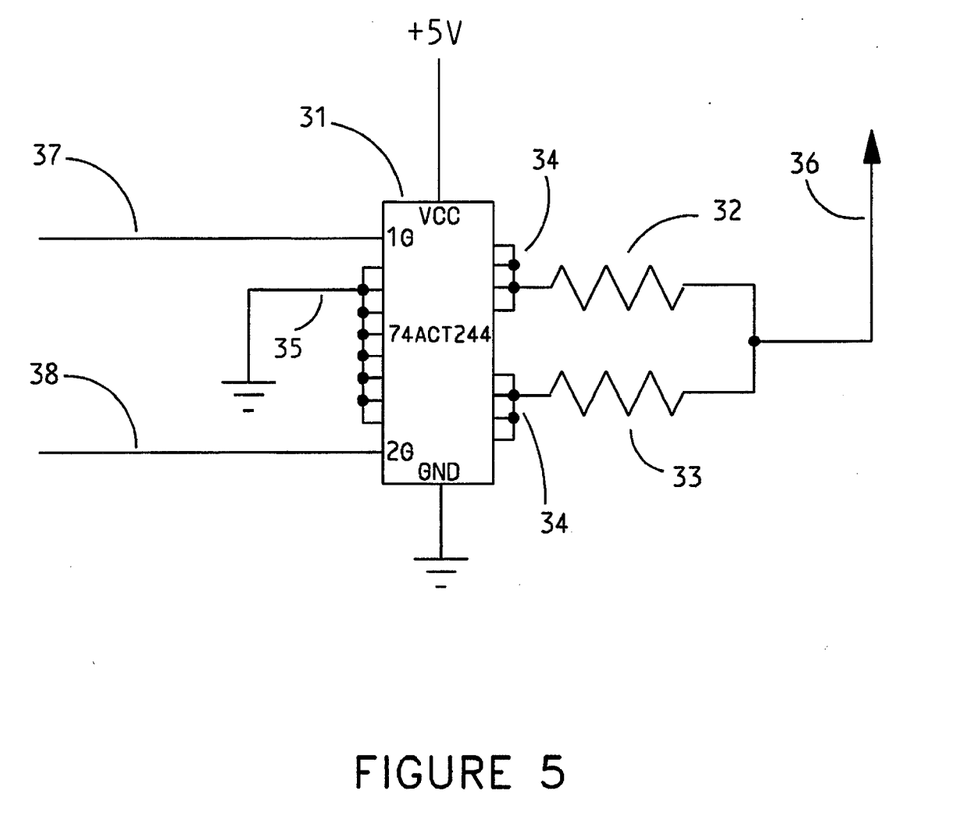
FIG. 5 is a schematic of an embodiment of the modulator.

FIG. 5 is a schematic diagram of a possible embodiment of part of the modulator. The control lines 37 and 38 come from the state machine PLD. These control lines are both high when the off state is desired. When the medium brightness state is desired, one of the lines is high, and one of the lines is low. When the full brightness state is desired, both lines are low. The control lines 37 and 38 are coupled to a 74ACT244 31 integrated circuit (a 74AC244 will also work). This circuit is normally used as a bus driver; however, when its control lines are high, its outputs 34 see a very high impedance to ground (tri-state). If its inputs are low (grounded) 35, and its control lines are low (enabled), its outputs 34 see a very low impedance to ground. Thus, this device performs very well in the role of a grounding switch.

The output line 36 is a current control lead of a constant current source similar to the LP2951 manufactured by Micrel (pin 7). This constant current device is used to drive the optical source in a manner where the amount of current on line 36 determines the brightness of the source. Two resistors 32 and 33 are placed in parallel with each other, but in series with line 36. These resistors are connected to the outputs of the 74ACT244 34. Thus, when both enable lines 37 and 38 are high, the 74ACT244 is open, and no current flows on line 36. This results in the off state for the optical source. When one of the enable lines, such as line 37 is low with the other enable line high, only one half of the 74ACT244 turns on, and current only flows through one resistor (32 in this example). In this state, the optical source is at half brightness. When both lines 37 and 38 are low, both halves of the 74ACT244 turn on, and current flows through the parallel combination of resistors 32 and 33. Here, the optical source is at high brightness. Controlling lines 37 and 38 from the state machine thus sets the state of brightness of the optical source. In this embodiment, there are only three brightness states; however, other similar modulators can be constructed that allow any number of brightness states. Also, any high quality analog switch can be substituted for the 74ACT244 without departing from the spirit and scope of the invention. The resistors 32 and 33 are chosen to achieve the desired brightness levels with the optical source in use. They are usually around 100 to 300 ohms.

Figure 6:
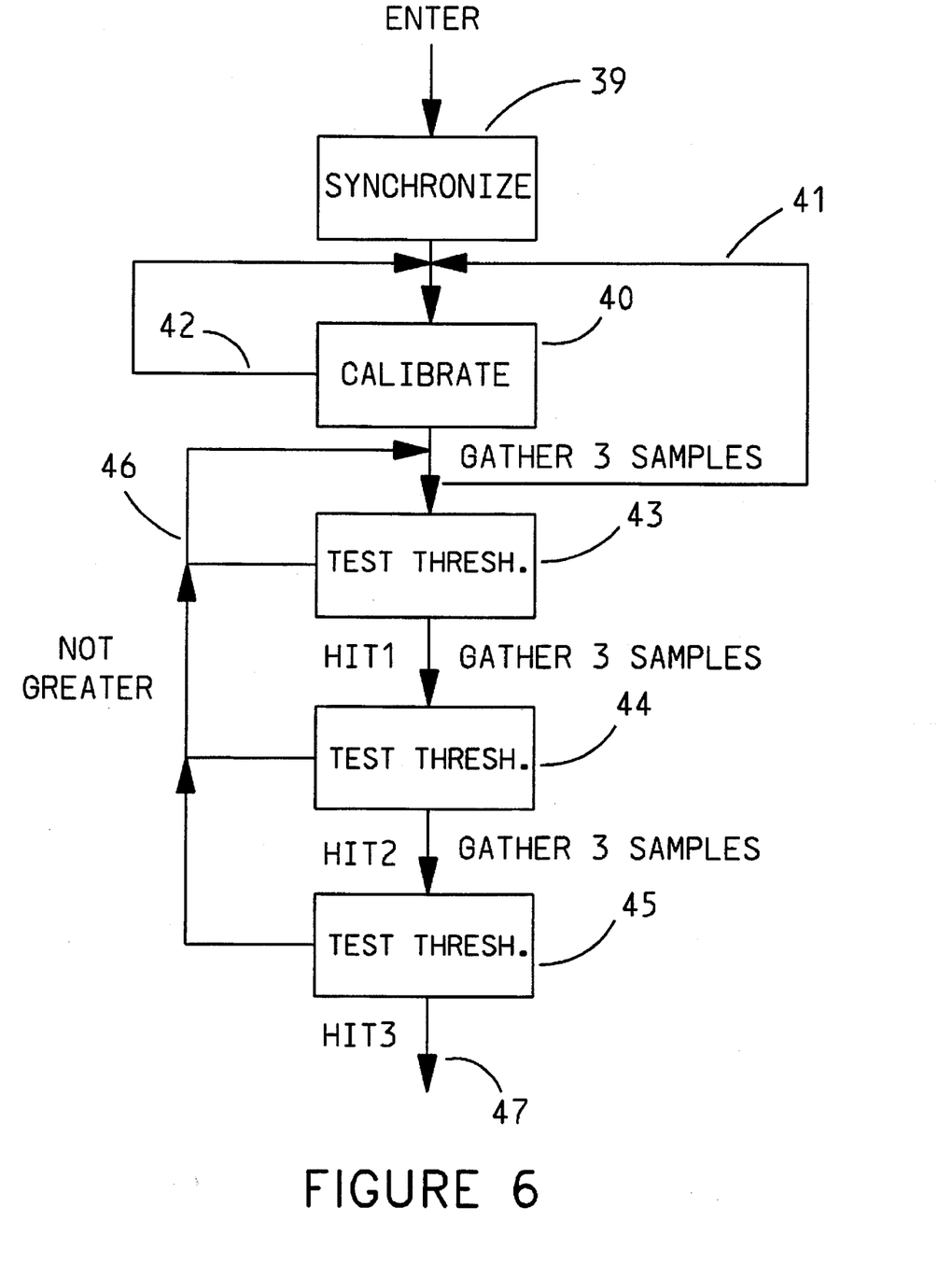
FIG. 6 is a flow chart of a possible detection program.

FIG. 6 is a flow chart of the program used to detect the application of liquid to the surface. It is assumed for the purposes of FIG. 6 that the A/D converter is providing one sample for every new modulated brightness level, and that there are three levels of brightness. When the program charted in FIG. 6 begins, it must wait for the first sample to come in and then decide which level it represents. Since ambient light can change any sample value, the program must take three samples (or all of the levels) to synchronize with the incoming data stream. The synchronization step 39 takes the first three samples (of different levels) that come in. It compares them and orders them by magnitude. From this ordering, it decides when the next sample representing the off level will come in. It then delays this many samples in order to synchronize. If the processor is used to control the generation of light levels, no synchronization is necessary.

After synchronization, the program continuously takes data samples in groups of three for this example. Before detection can take place, the program first must calibrate 40. This means to establish a baseline of the amount of ambient light present, and the differences between levels present. It must assume at this point that there is no liquid on the surface. If there is an extreme amount of ambient, the program may decide to wait to calibrate 42. If the ambient is reasonable, the program may simply average over several groups of like samples (samples representing the same levels) to establish a baseline, or it may begin a running average of each level or a running average of the differences between levels. The running average of differences has the advantage that it slowly tracks any long term drift in the system that does not represent application of liquid. If a fixed average is used, the program must re-calibrate from time to time to prevent false triggers from long term drift 41.

Once a baseline or running average is established, the program continues to take groups of three samples (or of the number of levels being used). With each new complete group, the newest differences are compared with the running average differences or the baseline differences to detect any major change. The absolute values of these comparisons of the differences are themselves compared against thresholds to determine a "hit" or condition where there is a major change in both differences. This is first done in step 43. Three more samples are taken, and again a "hit" is looked for in step 44. If no "hit" is found, the "hit" count is reset and the program acts as if no "hit" had occurred 46. If a second sequential "hit" is detected by step 44, three more samples are taken, and a third "hit" is checked for by step 45. If there is no third "hit", the count is reset and the program resumes as if no "hit" had occurred 46. If a third sequential "hit" is detected by step 45, a trigger is declared which means liquid has been detected. The routine exits 47 when a trigger is declared to either report it or perform some other part of the assay.

The statistics of three "hits" in a row eliminate random fluctuations and increase the probability of an accurate liquid detection. The use of a running average of differences allows more sensitive threshold settings without false triggering from long term drift. The three "hits" in a row method makes the system insensitive to fast flashes and transient motion of the chamber. The method of differences makes the invention robust in the presence of DC ambient light and 60 Hz (or 50 Hz) incandescent light.

Some surfaces have such high reflectivity that the optical detector may go into saturation on the brightest level. The present invention can compensate for this by ignoring the brightest level when it is greater than some predetermined absolute value. In this case, detection takes place on the differences between the remaining levels and the off level. The thresholds may be changed when this condition is detected. They are usually increased slightly to prevent false triggers, especially if there is only one remaining on level. As an alternative, the brightest level may be decreased in amplitude until it comes out of optical saturation. Such a dynamic decrease in the brightest light level is within the scope of the present invention and requires additional circuitry.

It is to be understood that the above-described arrangements are merely illustrative of the application of the principles of the invention and that other arrangements may be devised by those skilled in the art without departing from the spirit and scope of the invention.

What is claimed is:

1. An apparatus for detecting the application of liquid to an optical reflecting surface in the presence of ambient light, the invention comprising, in combination:

a light source;

electronic modulation means controlling the current to said light source to produce a plurality of intensity levels including one off level having no intensity;

an optical detector for producing electrical signals proportional to light intensity;

a reaction chamber containing a reflecting surface capable of receiving liquid, said surface positioned so that some light from the source reflects into the optical detector;

conversion means coupled to the optical detector, and synchronized to the modulation means, for producing at least one intensity sample for each of said intensity levels;

processing means for computing differences between intensity samples representing light levels and intensity samples representing the off level, said differences being proportional to reflectivity of the reflecting surface in the presence of ambient light;

reporting means for reporting the presence of liquid on the reflecting surface when said differences change by a predetermined amount.

2. The apparatus of claim 1 wherein the conversion means is an A/D converter.

3. The apparatus of claim 1 wherein the conversion means is an intensity to frequency converter.

4. The apparatus of claim 1 wherein the processing means determines ambient light intensity from intensity samples representing said off level.

5. The apparatus of claim 1 wherein the light source is a light emitting diode.

6. The apparatus of claim 5 wherein the light emitting diode emits infrared light.

7. The apparatus of claim 1 wherein the processing means is a microprocessor.

8. An apparatus for detecting the application of liquid to an optical reflecting surface in the presence of ambient light, said reflecting surface of the type used to perform coagulation assays, the invention comprising:

an optical source current modulated to at least one on amplitude level and one off level, said levels occurring at predetermined times;

a reaction chamber containing a reflecting surface and optical detector positioned so that light from the source reflects into the detector;

processing means responsive to amplitude levels from the optical detector for computing differences between the on amplitude levels and the off level, said differences representing reflectivity of the reflecting surface, and the off level representing ambient light, whereby said processor reports the application of liquid to the reflecting surface when said differences change by predetermined amounts.

9. An apparatus for detecting the application of liquid to a reflecting surface that is insensitive to ambient light and transient motion of the surface comprising:

an optical source producing light modulated to three different levels, an off level, a midrange level, and a bright level in sequence, each level being held for a predetermined duration;

an optical detector;

a reflecting surface capable of receiving liquid positioned such that light from the optical source reflects from the surface into the optical detector;

an A/D converter coupled to the optical detector and synchronized with the optical source producing one sample value for each modulated level in sequence;

processor means for determining an amount of ambient light from sample values of the off level, and surface reflectivity from a first difference of sample values of the bright level and sample values of the off level, and a second difference of the midrange level and the off level, the surface reflectivity being proportional to said differences;

a reporting means for reporting the application of liquid to the surface when said first difference and second difference change by predetermined amounts.

10. The apparatus of claim 9 wherein the processor means is a microcontroller.

11. The apparatus of claim 9 wherein the optical source is a light emitting diode.

12. The apparatus of claim 9 wherein the optical detector is a PIN diode.

13. The apparatus of claim 9 wherein the optical detector is an intensity to frequency converter.

14. A method of detecting the application of a liquid to a reflecting surface, said method being insensitive to ambient light and transient motion of the surface comprising, in combination:

current modulating an optical source at predetermined times to produce discrete amplitude levels with one level being an off level;

reflecting light from the optical source on a reflecting surface in a reaction chamber capable of receiving liquid, said light reflected into an optical detector with signal output;

sampling the signal output of said optical detector at least once for each different modulated level;

comparing differences between the modulated levels with the off level to determine an amount of ambient light and a change in reflectivity of the reflecting surface that can indicate application of liquid to the reaction chamber.

* * * * *